(12) United States Patent
Hennen et al.

(10) Patent No.: US 6,468,534 B1
(45) Date of Patent: Oct. 22, 2002

(54) METHODS FOR OBTAINING TRANSFER FACTOR FROM AVIAN SOURCES, COMPOSITIONS INCLUDING AVIAN-GENERATED TRANSFER FACTOR, AND METHODS OF USE

(75) Inventors: William J. Hennen, Springville; David T. Lisonbee, Orem, both of UT (US)

(73) Assignee: 4Life Research, LC, Provo, UT (US)

( * ) Notice: Subject to any disclaimer, the term of this patent is extended or adjusted under 35 U.S.C. 154(b) by 0 days.

(21) Appl. No.: 09/667,147

(22) Filed: Sep. 21, 2000

(51) Int. Cl.[7] .................. A61K 39/395; A61K 39/00; A61K 39/12; C12P 1/00; C07K 1/00

(52) U.S. Cl. .................. 424/157.1; 424/130.1; 424/184.1; 424/201.1; 424/227.1; 424/204.1; 435/41; 530/300; 530/350

(58) Field of Search .................. 514/21; 424/157.12, 424/130.1, 184.1, 201.1, 227.1, 278.1, 204.1, 214.1, 212.1, 230.1, 234.1; 530/300, 350; 435/41

(56) References Cited

U.S. PATENT DOCUMENTS

| | | | |
|---|---|---|---|
| 4,180,627 A | 12/1979 | Klesius et al. | 435/262 |
| 4,402,938 A | 9/1983 | Collins et al. | 424/85 |
| 4,816,563 A | 3/1989 | Wilson et al. | 530/344 |
| 5,080,895 A | 1/1992 | Tokoro | 424/85.8 |
| 5,367,054 A | * 11/1994 | Lee | 530/359 |
| 5,470,835 A | 11/1995 | Kirkpatrick et al. | 514/21 |
| 5,538,727 A | 7/1996 | Stolle et al. | 424/203.1 |
| 5,753,228 A | 5/1998 | Sterling et al. | 424/151.1 |
| 5,753,268 A | 5/1998 | Stolle et al. | 424/581 |
| 5,840,700 A | 11/1998 | Kirkpatrick et al. | 514/21 |
| 5,849,349 A | 12/1998 | Stolle et al. | 426/614 |
| 5,853,765 A | 12/1998 | Stolle et al. | 424/581 |

OTHER PUBLICATIONS

Fudenberg, H. H., et al., "Transfer Factor 1993: New Frontiers," *Progress in Drug Research*, vol. 42 (1994), pp. 309–318.

Qureshi, M.A., et al., "Understanding Immunology in Disease Development and Control," *Poultry Science*, vol. 77 (1998), pp. 1126–1129.

Sharma, J.M., "The Structure and Function of the Avian Immune System," *Acta Veterinaria Hungarica*, vol. 45(3) (1997), pp. 229–238.

Xlth International Congress on Transfer Factor, Universidad Autonoma de Nuevo Leon, Mar. 1999.

Egcel™ and BioChoice™, Overview for Health Care Professionals, DCV, Apr. 1999, pp. 1–4.

Millipore Sterile Membrane Filters, http://www.millipore.com. (2000).

Celite Filter Media; RH 1010, Funnel, Buchner Type; http://www.celtic–eng.com, http://www.glassfilter.com, http://www.worldminerals.com. (2000).

Fabio, Anthony di, "Scope of Protection Immune Milk." pp. 1–8, *The Arthritis Trust, Dedicated to Eradicating Rheumatoid Disease, from the Earth*, 2000.

(List continued on next page.)

Primary Examiner—Hankyel T. Park
Assistant Examiner—Stacy S. Brown
(74) Attorney, Agent, or Firm—TraskBritt

(57) ABSTRACT

A non-mammalian transfer factor, compositions including the non-mammalian transfer factor, and methods for generating and preparing the non-mammalian transfer factor. The non-mammalian transfer factor may have specificity for one or more antigens. A method of using the non-mammalian transfer factor includes administering either antigen-specific non-mammalian transfer factor or antigen non-specific non-mammalian transfer factor to mammals to treat or prevent pathogenic infections in the mammals.

30 Claims, 3 Drawing Sheets

OTHER PUBLICATIONS

Klesius et al., "Adoptive transfoer of Delayed Hypersensitivity and Protective Immunity to Elmeria Tenalta with Chicken–Derived Transfer Factor,"pp. 1333–1337, *Poultry Science*, vol. 63, 1984.

Glambrone et al., "Adoptive Transfer of Delayed Wattle Reactivity in Chickens wiht a Dialyzable Leukocyte Extract Containing Transfer Factor," pp. 767–771, *Poultry Science*, vol. 62, 1983.

* cited by examiner

METHODS FOR OBTAINING TRANSFER FACTOR FROM AVIAN SOURCES, COMPOSITIONS INCLUDING AVIAN-GENERATED TRANSFER FACTOR, AND METHODS OF USE

BACKGROUND OF THE INVENTION

1. Field of the Invention

The present invention relates generally to methods for generating antigen-specific transfer factor, compositions including such antigen-specific transfer factor, and uses of these compositions. In particular, the present invention relates to methods for generating antigen-specific transfer factor in an avian host and obtaining the antigen-specific transfer factor from eggs.

2. Background of Related Art

Many deadly pathogens are passed to humans from the animal kingdom. For example, monkeys are the sources of the type I human immunodeficiency virus (HIV-I), which causes acquired immune deficiency syndrome (AIDS) and monkeypox, which is similar to smallpox; ground-dwelling mammals are believed to be the source of the Ebola virus; fruit bats and pigs are the source of the Nipah virus; the Hendra virus comes from horses; the "Hong Kong Flu" originated in chickens; and wild birds, especially ducks, are the sources of many of the deadly influenza viruses. Many diseases also have animal reservoirs. By way of example, mice carry Hanta virus, rats carry the Black Plague, and deer carry Lyme disease.

The Immune System

The immune systems of vertebrates are equipped to recognize and defend the body from invading pathogenic organisms, such as parasites, bacteria, fungi, and viruses. Vertebrate immune systems typically include a cellular component and a noncellular component.

The cellular component of an immune system includes the so-called lymphocytes, or white blood cells, of which there are several types. It is the cellular component of a mature immune system that typically mounts a primary, nonspecific response to invading pathogens, as well as being involved in a secondary, specific response to pathogens.

In the primary, or initial, response to an infection by a pathogen, white blood cells that are known as phagocytes locate and attack the invading pathogens. Typically, a phagocyte will internalize, or "eat" a pathogen, then digest the pathogen. In addition, white blood cells produce and excrete chemicals in response to pathogenic infections that are intended to attack the pathogens or assist in directing the attack on pathogens.

Only if an infection by invading pathogens continues to elude the primary immune response is a specific, secondary immune response to the pathogen needed. As this secondary immune response is typically delayed, it is also known as "delayed-type hypersensitivity". A mammal, on its own, will typically not elicit a secondary immune response to a pathogen until about seven (7) to about fourteen (14) days after becoming infected with the pathogen. The secondary immune response is also referred to as an acquired immunity to specific pathogens. Pathogens have one or more characteristic proteins, which are referred to as "antigens". In a secondary immune response, white blood cells known as B lymphocytes, or "B-cells", and T lymphocytes, or "T-cells", "learn" to recognize one or more of the antigens of a pathogen. The B-cells and T-cells work together to generate proteins called "antibodies", which are specific for one or more certain antigens on a pathogen.

The T-cells are primarily responsible for the secondary, or delayed-type hypersensitivity, immune response to a pathogen or antigenic agent. There are three types of T-cells: T-helper cells, T-suppressor cells, and antigen-specific T-cells, which are also referred to as cytotoxic (meaning "cell-killing") T-lymphocytes ("CTLs"), or T-killer cells. The T-helper and T-suppressor cells, while not specific for certain antigens, perform conditioning functions (e.g., the inflammation that typically accompanies an infection) that assist in the removal of pathogens or antigenic agents from an infected host.

Antibodies, which make up only a part of the noncellular component of an immune system, recognize specific antigens and, thus, are said to be "antigen-specific". The generated antibodies then basically assist the white blood cells in locating and eliminating the pathogen from the body. Typically, once a white blood cell has generated an antibody against a pathogen, the white blood cell and all of its progenitors continue to produce the antibody. After an infection is eliminated, a small number of T-cells and B-cells that correspond to the recognized antigens are retained in a "resting" state. When the corresponding pathogenic or antigenic agents again infect the host, the "resting" T-cells and B-cells activate and, within about forty-eight (48) hours, induce a rapid immune response. By responding in this manner, the immune system mounts a secondary immune response to a pathogen, the immune system is said to have a "memory" for that pathogen.

Mammalian immune systems are also known to produce smaller proteins, known as "transfer factors," as part of a secondary immune response to infecting pathogens. Transfer factors are another noncellular part of a mammalian immune system. Antigen-specific transfer factors are believed to be structurally analogous to antibodies, but on a much smaller molecular scale. Both antigen-specific transfer factors and antibodies include antigen-specific cites and both include highly conserved regions that interact with receptor sites on their respective effector cells. In transfer factor and antibody molecules, a third, "linker", region connects the antigen-specific cites and the highly conserved regions.

The Role of Transfer Factor in the Immune System

Transfer factor is a low molecular weight isolate of lymphocytes. Narrowly, transfer factors may have specificity for single antigens. U.S. Pat. Nos. 5,840,700 and 5,470,835, both of which issued to Kirkpatrick et al. (hereinafter collectively referred to as "the Kirkpatrick Patents"), disclose the isolation of transfer factors that are specific for certain antigens. More broadly, "specific" transfer factors have been generated from cell cultures of monoclonal lymphocytes. Even if these transfer factors are generated against a single pathogen, they have specificity for a variety of antigenic sites of that pathogen. Thus, these transfer factors are said to be "pathogen-specific" rather than antigen-specific. Similarly, transfer factors that are obtained from a host that has been infected with a certain pathogen are pathogen-specific. Although such preparations are often referred to in the art as being "antigen-specific" due to their ability to elicit a secondary immune response when a particular antigen is present, transfer factors having different specificities may also be present. Thus, even the so-called "antigen-specific", pathogen-specific transfer factor preparations may be specific for a variety of antigens.

Additionally, it is believed that antigen-specific and pathogen-specific transfer factors may cause a host to elicit a delayed-type hypersensitivity immune response to pathogens or antigens for which such transfer factor molecules are not specific. Transfer factor "draws" at least the non-specific T-cells, the T-inducer and T-suppressor cells, to an infecting pathogen or antigenic agent to facilitate a secondary, or delayed-type hypersensitivity, immune response to the infecting pathogen or antigenic agent.

Typically, transfer factor includes an isolate of proteins obtained from immunologically active mammalian sources and having molecular weights of less than about 10,000 daltons (D). It is known that transfer factor, when added either in vitro or in vivo to mammalian immune cell systems, improves or normalizes the response of the recipient mammalian immune system.

The immune systems of newborns have typically not developed, or "matured", enough to effectively defend the newborn from invading pathogens. Moreover, prior to birth, many mammals are protected from a wide range of pathogens by their mothers. Thus, many newborn mammals cannot immediately elicit a secondary response to a variety of pathogens. Rather, newborn mammals are typically given secondary immunity to pathogens by their mothers. One way in which mothers are known to boost the immune systems of newborns is by providing the newborn with a set of transfer factors. In mammals, transfer factor is provided by a mother to a newborn in colostrum, which is typically replaced by the mother's milk after a day or two. Transfer factor basically transfers the mother's acquired, specific (i.e., delayed-type hypersensitive) immunity to the newborn. This transferred immunity typically conditions the cells of the newborn's immune system to react against pathogens in an antigen-specific manner, as well as in an antigen- or pathogen-nonspecific fashion, until the newborn's immune system is able on its own to defend the newborn from pathogens. Thus, when transfer factor is present, the immune system of the newborn is conditioned to react to pathogens with a hypersensitive response, such as that which occurs with a typical delayed-type hypersensitivity response. Accordingly, transfer factor is said to "jump start" the responsiveness of immune systems to pathogens.

Much of the research involving transfer factor has been conducted in recent years. Currently, it is believed that transfer factor is a protein with a length of about forty-four (44) amino acids. Transfer factor is believed to have a molecular weight in the range of about 4,000 to about 5,000 Daltons (D), or about 4 kD to about 5 kD. Transfer factor is also believed to include three functional fractions: an inducer fraction; an immune suppressor fraction; and an antigen-specific fraction. Many in the art believe that transfer factor also includes a nucleoside portion, which could be connected to the protein molecule or separate therefrom, that may enhance the ability of transfer factor to cause a mammalian immune system to elicit a secondary immune response. The nucleoside portion may be part of the inducer or suppressor fractions of transfer factor.

The antigen-specific region of the antigen-specific transfer factors is believed to comprise about eight (8) to about twelve (12) amino acids. A second highly-conserved region of about ten (10) amino acids is thought to be a very high-affinity T-cell receptor binding region. The remaining amino acids may serve to link the two active regions or may have additional, as yet undiscovered properties. The antigen-specific region of a transfer factor molecule, which is analogous to the known antigen-specific structure of antibodies, but on a much smaller molecular weight scale, appears to be hyper-variable and is adapted to recognize a characteristic protein on one or more pathogens. The inducer and immune suppressor fractions are believed to impart transfer factor with its ability to condition the various cells of the immune system so that the cells are more fully responsive to the pathogenic stimuli in their environment.

Sources of Noncellular Immune System Components

Conventionally, transfer factor has been obtained from the colostrum of milk cows. While milk cows typically produce large amounts of colostrum and, thus, large amounts of transfer factor over a relatively short period of time, milk cows only produce colostrum for about a day or a day-and-a-half every year. Thus, milk cows are neither a constant source of transfer factor nor an efficient source of transfer factor.

Transfer factor has also been obtained from a wide variety of other mammalian sources. For example, in researching transfer factor, mice have been used as a source for transfer factor. Antigens are typically introduced subcutaneously into mice, which are then sacrificed following a delayed-type hypersensitivity reaction to the antigens. Transfer factor is then obtained from spleen cells of the mice.

While different mechanisms are typically used to generate the production of antibodies, the original source for antibodies may also be mammalian. For example, monoclonal antibodies may be obtained by injecting a mouse, rabbit, or other mammal with an antigen, obtaining antibody-producing cells from the mammal, then fusing the antibody-producing cells with immortalized cells to produce a hybridoma cell line, which will continue to produce the monoclonal antibodies throughout several generations of cells and, thus, for long periods of time.

Antibodies against mammalian pathogens have been obtained from a wide variety of sources, including mice, rabbits, pigs, cows, and other mammals. In addition, the pathogens that cause some human diseases, such as the common cold, are known to originate in birds. As it has become recognized that avian (i.e., bird) immune systems and mammalian immune systems are very similar, some researchers have turned to birds as a source for generating antibodies.

U.S. Pat. No. 5,080,895, issued to Tokoro on Jan. 14, 1992 (hereinafter "the '895 Patent"), discloses a method that includes injecting hens with pathogens that cause intestinal infectious diseases in neonatal mammals. The hens then produce antibodies that are specific for these pathogens, which are present in eggs laid by the hens. The '895 Patent discloses compositions that include these pathogen-specific antibodies and use thereof to treat and prevent intestinal diseases in neonatal piglets and calves. In addition, the '895 Patent assumes that a pathogen-specific transfer factor-like substance is passed from a hen to her eggs. Nonetheless, the '895 Patent does not disclose that such a transfer factor-like substance was in fact present in the eggs, or that an antibody-free composition derived from eggs that were assumed to contain this transfer factor-like substance actually treated or prevented intestinal diseases in neonatal mammals. In fact, the '895 Patent discloses the use of a filter with about 0.45 $\mu$m diameter holes to isolate transfer factor from antibodies. As those of skill in the art are aware, however, antibodies, larger molecules, viruses, and even some bacteria will pass through the pores of a 0.45 $\mu$m filter. In reality, it is not likely that any individual protein molecules having molecular weights of less than about 12,000 D were separated by such a filter. Based on the pore size of the filter used, however, it is more likely that no individual protein molecules, including antibodies, were removed by the filter.

Avian antibodies that are specific for mammalian pathogens have also been obtained by introducing antigens into eggs.

Treatment of pathogenic infections in mammals with avian antibodies is typically not desirable, however, since the immune systems of mammals are likely to respond negatively to the large avian antibody molecules by eliciting an immune response to the antibodies themselves. Moreover, as mammalian immune systems do not recognize avian antibodies as useful for their abilities to recognize certain pathogens, or the specificities of avian antibodies for antigens of such pathogens, avian antibodies do not even elicit the desired immune responses in mammals.

The inventors are not aware of any art that teaches a method for generating transfer factor in a non-mammalian source, an efficient method for obtaining transfer factor from such a non-mammalian source, such as an avian source, or a method for using such transfer factor in treating or preventing infections by pathogens.

SUMMARY OF THE INVENTION

The present invention includes a method for generating the production of transfer factor in a non-mammalian source and obtaining transfer factor from a non-mammalian source. In addition, compositions including non-mammalian transfer factor are also within the scope of the present invention, as are methods of using these compositions.

The non-mammalian transfer factor generated, obtained, and used in accordance with the present invention may either be antigen non-specific or antigen-specific (i.e., configured to bind or recognize one or more antigens). Unless otherwise indicated, the term "transfer factor", as used herein, includes the previously discussed broad definition, which includes each of the various types of transfer factors, including pathogen-specific, antigen-specific, and transfer factors that are not specific for particular pathogens or antigenic agents. The term "non-specific", when used herein with respect to transfer factors, refers to both transfer factors that are not specific for particular antigens and to mixtures that include transfer factors with different antigen specificities.

Non-specific transfer factor includes transfer factor that the non-mammalian source animal already produces. Individual non-specific transfer factor molecules that are produced by the source animal may have specificity for various antigenic agents, including pathogens, that are present in the source animal's environment. Nonetheless, for purposes of the present invention, transfer factor that is generated merely by a source animal's reaction to its environment is referred to as "non-specific".

On the other hand, antigen-specific transfer factor is generated by exposing a non-mammalian source animal to one or more antigens. The antigens of various types of pathogens, including, but not limited to, bacteria, viruses, fungi, and parasites, have been found by the inventors to induce the production of non-specific transfer factor in non-mammalian sources. Antigen-specific transfer factor has been generated by non-mammalian source animals by both natural antigens (including from live, inactivated, and attenuated sources) and synthetic antigens.

The production of transfer factor in a non-mammalian source may be induced by introducing an antigen characteristic of a certain pathogen into a female non-mammalian source animal. Exemplary types of source animals that may be used include, without limiting the scope of the present invention, birds, reptiles, amphibians, and fish. Preferably, the non-mammalian source animal produces eggs on a frequent basis. Thus, for purposes of the present invention, hens are particularly useful as the non-mammalian source animal. These non-mammalian source animals produce transfer factor, which then appears in the eggs of these source animals. Alternatively, an egg of a non-mammalian source animal may be exposed to the antigenic agent (e.g., by injection of the antigenic agent into the egg) to induce production of transfer factor by the egg itself.

The transfer factor generated by a non-mammalian source animal or by the egg of a non-mammalian source animal may be recovered from the egg and separated from other constituents of the egg, including proteins of larger molecular weight, such as antibodies. Alternatively, transfer factor may be purified from one or more eggs of a non-mammalian source animal.

The non-mammalian transfer factor may then be incorporated into a composition or apparatus for administration to a mammalian or non-mammalian subject or administered directly to the subject. The non-mammalian transfer factor or compositions including the non-mammalian transfer factor may be administered enterally (i.e., orally), or parenterally (i.e., by a non-oral route, such as by injection, through the skin, etc.). Administration of both non-specific and specific non-mammalian transfer factors have been found to initiate an early, specific (i.e., secondary) immune response in mammals to various invading pathogens. Thus, non-mammalian transfer factor has been found to be useful in treating and preventing diseases that may be caused by these various pathogens.

Other features and advantages of the present invention will become apparent to those of skill in the art through consideration of the ensuing description, the accompanying drawings, and the appended claims.

BRIEF DESCRIPTION OF THE DRAWINGS

In the drawings, which illustrate exemplary embodiments of the present invention.

DETAILED DESCRIPTION OF THE INVENTION

As explained previously herein, mammalian mothers pass transfer factor to their newborn children in the colostrum, which is replaced by mother's milk after about a day or two. The transfer factor present in colostrum transfers delayed-type hypersensitivity for certain antigens to the child, thus "jump-starting" the ability of the immune system of the newborn child to respond to certain pathogens, if the child becomes infected with these pathogens.

Over recent years, it has been discovered that avian (i.e., bird) immune systems are very similar to those of mammals. In fact, early studies of the components of immune systems were performed on birds. As a result of these early studies of immune systems, B-cells, one of the types of white blood cells discussed previously herein, was so named due to its origin in the bursa of birds. In addition, it is known that various infectious agents, including some viruses that cause the common cold and influenza A virus, originate in birds and are passed onto humans.

As avian immune systems bear some resemblances to the immune systems of mammals, the inventors believe that transfer factor is also a component of avian immune systems, as well as of the immune systems of other non-mammalian vertebrates. In addition, the inventors believe that although non-mammalian mothers do not provide colostrum to their newborn children, these animals could still transfer immunity to their children by way of transfer factor. In birds and other egg-laying vertebrates, the mother's primary opportunity to provide transfer factor to her children is in the egg-yolk, which supplies the growing embryo with the necessary nutrients during growth. Thus, the inventors have long believed that antigen non-specific and antigen-specific transfer factor could be obtained from eggs.

Figure 1:
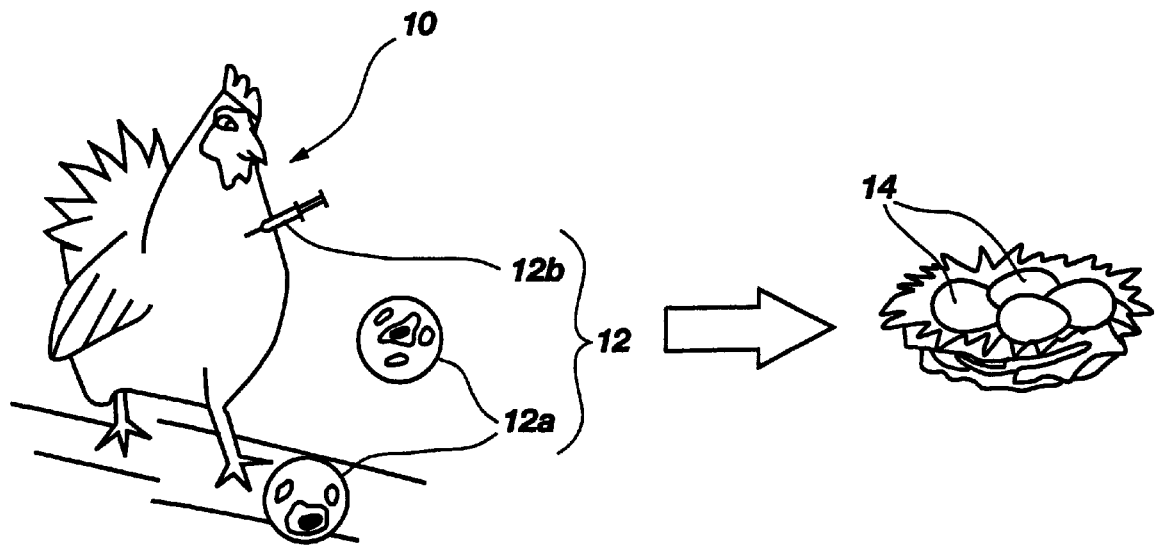
FIG. 1 is a schematic representation of an exemplary method for generating non-mammalian transfer factor in a non-mammalian source animal.

FIG. 1 schematically illustrates a method for obtaining desired transfer factor from a non-mammalian source 10 of transfer factor, in this case a hen. Non-mammalian source 10 may be exposed to environmental antigenic agents 12a or exposed to specific antigenic agents 12b. Non-mammalian source 10 may be exposed to specific antigenic agents 12b by injection, orally, or otherwise, as known in the art. Non-mammalian source 10 may be exposed to antigenic agents 12b either with or without an adjuvant present. Such exposure to specific antigenic agents 12b may occur once or be repeated. For simplicity, antigenic agents 12a and 12b are also referred to herein as antigenic agents 12 or simply as antigens.

Figure 2:
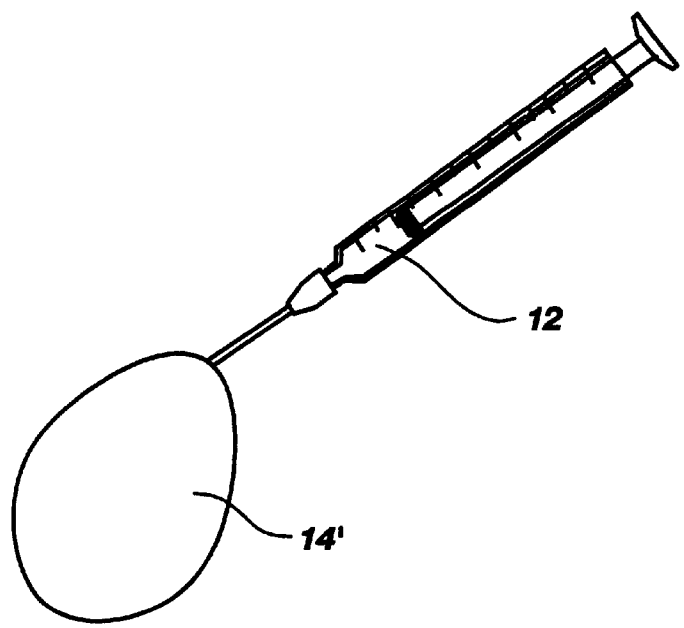
FIG. 2 is a schematic representation of an exemplary method for generating non-mammalian transfer factor directly in the eggs of a non-mammalian source animal.

Alternatively, with reference to FIG. 2, an egg 14' of a non-mammalian animal may be directly exposed to one or more antigenic agents 12, such as by injection or otherwise, as known in the art.

Figure 3:
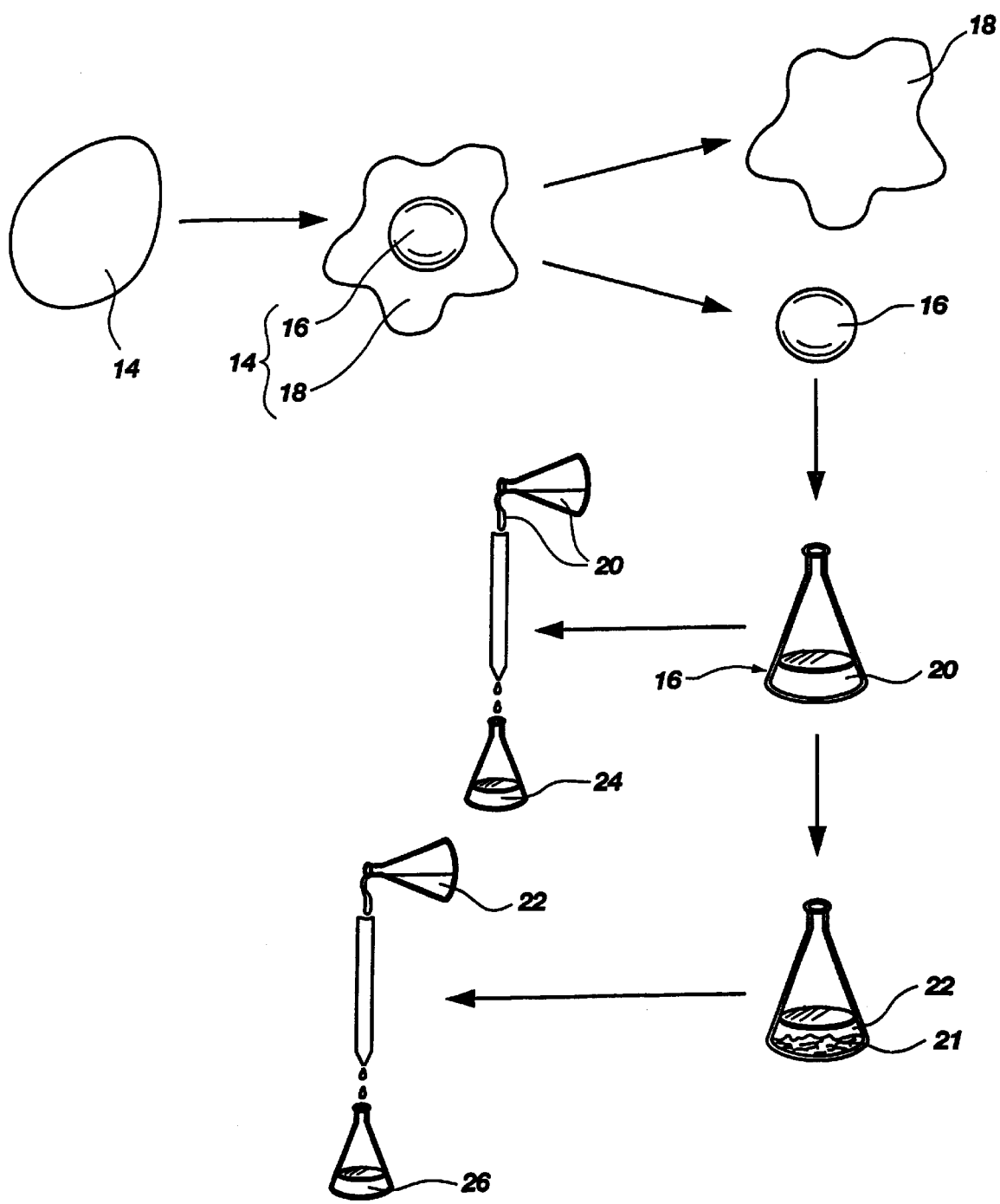
FIG. 3 is a schematic representation of an exemplary method for obtaining non-mammalian transfer factor from eggs.

With reference to FIG. 3, after non-mammalian source 10 or non-mammalian eggs 14' that were directly exposed to one or more antigenic agents 12 have been given an adequate opportunity to elicit a secondary, or delayed-type hypersensitivity, immune response to antigenic agents 12, eggs 14 are collected. The yolks 16 and whites 18 of eggs 14 are then separated from one another, and various filtration processes are conducted on yolks 16 to obtain a water soluble fraction 20 thereof that includes transfer factor. Larger molecular weight proteins, such as antibodies, may also be removed from water soluble fraction 20 of yolks 16 by known processes, such as by filtering on the basis of molecular weight or by causing these larger molecular weight proteins to precipitate out of solution (e.g., in cold ethyl alcohol), then removing the precipitate 21 from water soluble fraction 20 (e.g., by filtration) to provide a substantially antibody-free, transfer factor-containing solution 22. Alternatively, the yolks 16 and whites 18 need not be separated.

In addition, antigen-specific non-mammalian transfer factor present in water soluble fraction 20 of yolks 16 or in or in solution 22 may be substantially purified from other constituents of water soluble fraction 20 or solution 22 by known techniques, such as by use of the gel permeation and affinity chromatography techniques disclosed in U.S. Pat. Nos. 5,840,700 and 5,470,835, both of which issued to Kirkpatrick et al. (hereinafter collectively referred to as "the Kirkpatrick Patents"), the disclosures of both of which are hereby incorporated by this reference in their entireties. The technique disclosed in the Kirkpatrick Patents is used to isolate biomolecules, such as transfer factor and antibodies, from the other constituents of a solution on the basis of the specificity of these biomolecules for one or more antigens or other specific binding agents. Thus, when the technique disclosed in the Kirkpatrick Patents is used on the antibody- and transfer factor-containing water soluble fraction 20 of egg yolk 16, both transfer factor and antibody may be isolated from the remainder of water soluble fraction 20 with the resulting solution 24 including both antibody and transfer factor. If, on the other hand, the technique disclosed in the Kirkpatrick Patents is conducted on a substantially antibody-free, transfer factor-containing solution 22, the product will be a substantially pure solution 26 of transfer factor specific for one or more antigens. Of course, other methods for obtaining transfer factor from eggs are also within the scope of the present invention, including methods for obtaining transfer factor from various egg preparations, including powdered or freeze-dried whole eggs or egg yolks.

Figure 4:
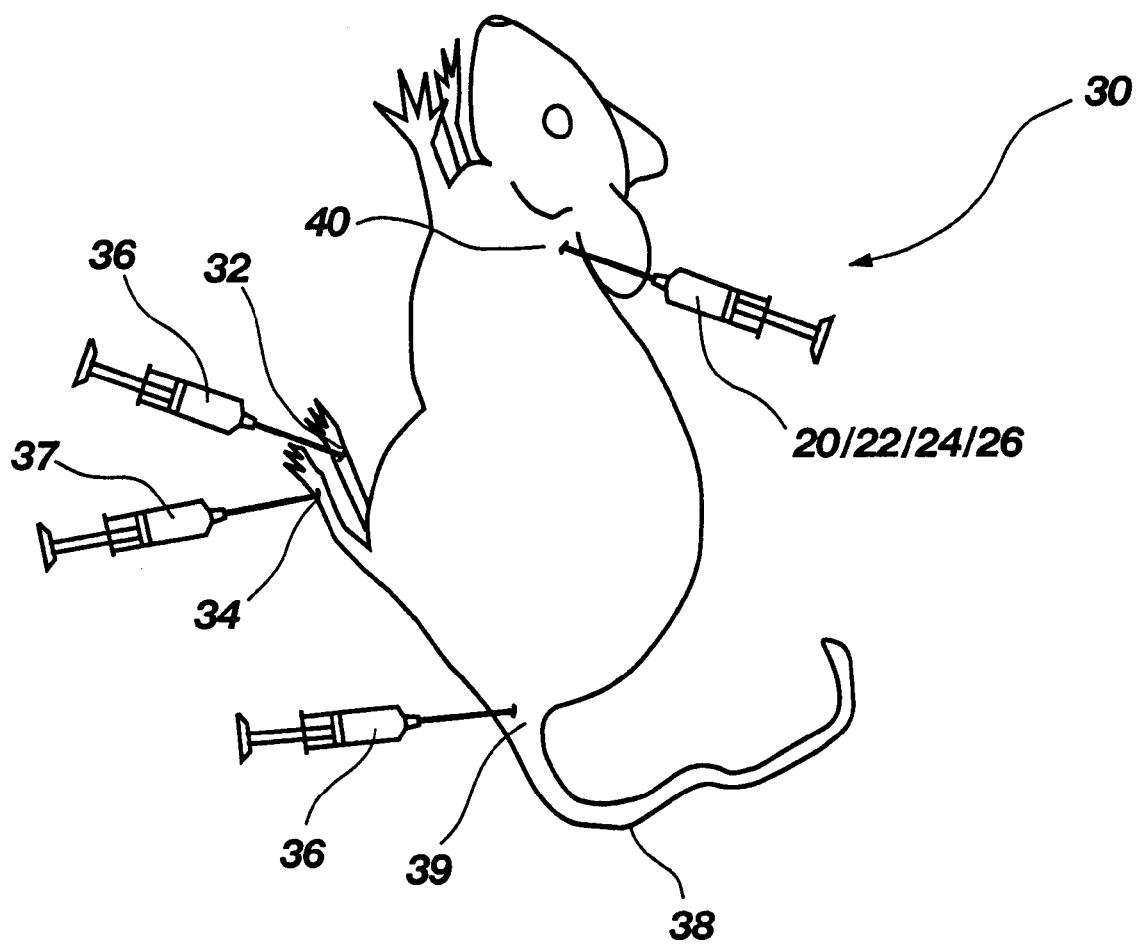
FIG. 4 is a schematic representation of an exemplary method for testing for the presence of transfer factor in a solution and for using transfer factor to prevent infection by pathogens or to treat pathogenic infections.

Referring now to FIG. 4, an exemplary method for testing for the presence of non-mammalian transfer factor specific for one or more antigens in a solution, known as a mouse footpad assay, is schematically depicted.

About seven (7) days prior to testing the effectiveness of avian transfer factor in causing mice to elicit a secondary immune response to a particular antigen or pathogen for which the avian transfer factor was specific, a positive control population of six female BALB/c mice is prepared. Each mouse 30 of the positive control population, having ages of about nine (9) weeks to about ten (10) weeks, is anesthetized with isoflurane. About 0.02 ml of a 50/50 (wt/wt) mixture of Freund's adjuvant and the particular antigen 36 against which the avian transfer factor to be tested is specific is administered to each mouse 30 by way of two intramuscular injections, one injection at each side of the base 39 of the tail 38. As these injections are conducted about seven (7) days prior to conducting the mouse footpad assay, the mice of the positive control population are permitted to generate their own secondary, or delayed-type hypersensitivity response to antigen 36.

About twenty-four (24) hours prior to the mouse footpad test, the mice of a first test population, which also includes six female BALB/c mice that are about nine (9) to about ten (10) weeks old (i.e., about the same age as the mice of the positive control population), are also anesthetized with isoflurane. About 0.5 ml of a solution 20, 24 including a preparation containing both avian transfer factor and avian antibody, reconstituted in distilled water, is then administered by subcutaneous injection at the back of the neck 40 of each mouse 30 of the first test population. By comparing the results obtained from these mice with the results obtained from mice of a second test population that had been treated with a substantially antibody-free preparation, the relative contributions of transfer factor and antibody to the swelling could be determined. As antibodies do not elicit a secondary immune response, it was believed prior to conducting the experiments described herein that the measure of the secondary immune response in the first and second test populations of mice would be very similar.

Each mouse of the second test population that includes six female BALB/c mice, having ages of about nine (9) to about ten (10) weeks old (i.e., about the same age as the mice of the positive control and first test populations), are also anesthetized with isoflurane. Each of the six mice 30 is given, by subcutaneous injection in the back of the neck 40, about 0.5 ml of a solution 22, 26 including, reconstituted in distilled water, a lyophilized antigen-specific avian transfer factor preparation with substantially no antibodies.

A negative control population also includes six female BALB/c mice of about nine (9) to about ten (10) weeks in age (i.e., about the same ages as the other three populations of mice).

In order to conduct the mouse footpad assay, the mice of each of the four populations are anesthetized and the distances across each of the largest right hind footpad 32 and the largest left hind footpad 34 of each mouse 30 are measured, such as with a Starrett gauge. Right hind footpad 32 is then subcutaneously injected with an antigen 36-containing solution. Left hind footpad 34, which is used as a control, is injected with about the same volume of a control solution 37, such as a sterile saline diluent, as the volume of solution that is injected into right hind footpad 32.

After a sufficient amount of time (e.g., about sixteen (16) to about twenty-four (24) hours) has elapsed, each mouse 30 is again anesthetized and the distances across right and left hind footpads 32, 34 are again measured. A significant amount of swelling, determined by an increase in the distances across a right hind footpad 32 of mouse 30, is indicative of the occurrence of a delayed-type hypersensitivity reaction in that footpad 32.

Of course, different solutions 24, 26 including transfer factors with specificities for different antigens may be tested on different sets of mice to detect any differences in the abilities of these solutions to transfer delayed-type hypersensitivity immunity to the mice. In addition, the results for each solution may be compared to those obtained from positive control and negative control populations of mice 30. If significant swelling occurs in the right hind footpads 34 of mice 30 to which a substantially antibody-free solution, such as solution 22 or solution 26 of FIG. 3, was administered, the delayed-type hypersensitivity that causes such swelling is attributed to the administered transfer factor.

The following examples are merely illustrative of embodiments of methods for generating, obtaining, and using transfer factor that incorporate teachings of the present invention:

EXAMPLE 1

Transfer factor specific for Newcastle Virus was generated by exposing day-old chicks to a coarse spray of infectious bronchitis/Newcastle virus (IBNC) vaccine, as known in the art, at zero (0) days, forty-two (42) days, and eighty-four (84) days. Eggs laid by these five hens at about one-hundred seventy-five (175) days following the first IBNC vaccine injection were collected.

EXAMPLE 2

The yolks from a first sampling of the antigen specific transfer factor-containing eggs generated in EXAMPLE 1 were separated from the whites, diluted about six (6) to about nine (9) times, by volume, in deionized water (i.e., about one (1) part egg white mixed with about five (5) parts water to about eight (8) parts water) and frozen. The lipid layer from these frozen egg yolks was mechanically separated from the water-soluble fraction of the egg yolks. This water-soluble fraction was then permitted to thaw to a temperature of about 4° C. to about 6° C. and vacuum filtered by use of Whatman qualitative filter paper using a 55 mm diameter porcelain Büchner funnel. The filtrate was then vacuum filtered through a glass microfiber filter, again using a 55 mm diameter Büchner funnel.

A third filtration was then conducted to collect proteins and to remove lipids and lipoproteins from the solution. The third filtration was effected by way of a DURAPORE hydrophilic membrane. The protein-containing fraction, which included both transfer factor and antibody specific for the infectious bronchitis pathogen and Newcastle Virus was collected, frozen, and lyophilized, or freeze-dried, as known in the art.

EXAMPLE 3

The water-soluble fractions of diluted yolk preparations from a second sampling of the eggs collected in EXAMPLE 1 were again mechanically separated from the lipid portions thereof and filtered, as explained previously herein in EXAMPLE 2.

In accordance with the method disclosed in U.S. Pat. No. 4,180,627, which issued to Klesius et al., the disclosure of which is hereby incorporated by this reference in its entirety, an adequate volume of ethyl alcohol (EtOH), or ethanol, was added to the protein-containing fraction to dilute the ethyl alcohol to a concentration of about 60% of the total volume of the alcohol-protein fraction solution. This solution was then cooled to a temperature of about 4 to about 6° C. for a long enough period of time (e.g., overnight, or for about 10–12 hours) for larger molecular weight proteins, including antibodies, present in the solution to precipitate from the solution. Smaller molecular weight proteins (e.g., proteins having molecular weights of about 8,000 D or less), including any transfer factor from the egg yolks, remained in solution.

The larger molecular weight protein-containing precipitate was then removed from the solution by filtering the solution through a Whatman glass microfiber filter in a 55 mm diameter Büchner funnel. CELITE®, a diatomite, or diatomaceous earth, filtration aid available from Celite Corporation of Lompoc, Calif., was used to prevent the precipitate from clogging the filter during filtration of the solution. This substantially precipitate-free solution was then collected, frozen, and lyophilized, as known in the art.

EXAMPLE 4

Each mouse of a test population that included three BALB/c mice, each having an age in the range of about nine (9) to about ten (10) weeks, was tested to determine whether the IBNV-specific avian transfer factor would impart an early secondary, or delayed-type hypersensitivity, immune response to the mice. Each mouse was anesthetized with isoflurane. The distances across the largest footpads of both the left and right hind feet of each mouse were then measured with a Starrett gauge. Each mouse was then given a subcutaneous injection in the back of the neck of about 0.5 ml of a solution that included about 16%, by weight, of the IBNV-specific avian transfer factor reconstituted in distilled water.

After about twenty-four (24) hours, each of the mice was again anesthetized with isoflurane. About 0.01 ml of a sterile saline diluent was then injected into the largest footpad of the left hind foot of each mouse, which footpad served as a control, while the largest footpad of the right hind foot of each mouse was injected with about 0.01 ml of a solution including about 10,000 doses of Newcastle-Bronchitis vaccine reconstituted in about 250 ml of distilled water.

Before another twenty-four (24) hours had elapsed, one of the mice (Mouse #1) died. The two remaining mice were again anesthetized with isoflurane and the largest footpads on their hind feet were again measured. The results follow:

TABLE 1

Newcastle Virus-Test Population

| | Footpad size (μm): | | |
|---|---|---|---|
| | Before Sample Injection | Final | Difference |
| Mouse #1 | | | |
| Left Foot (Control) | 1250 | | |
| Right Foot (Test) | 2151 | | |
| Mouse #2 | | | |
| Left Foot (Control) | 2180 | 2350 | 50 |
| Right Foot (Test), | 2165 | 2440 | 85 |
| Mouse #3 | | | |
| Left Foot (Control) | 2145 | 2160 | 15 |
| Right Foot (Test) | 2110 | 2200 | 90 |

The greater increase in size, or swelling, of the right footpad (increases of 85 μm and 90 μm) over that of the left footpad (increases of 50 μm and 15 μm, respectively) indicates that the IBNV-specific avian transfer factor-containing solution induced a delayed-type hypersensitivity reaction in the right feet of Mouse #2 and Mouse #3 within about twenty-four hours following the introduction of the Newcastle-Bronchitis vaccine.

In the remaining examples, substantially the same methods as those disclosed in EXAMPLES 1–3 were used to generate avian transfer factors specific for different types of antigens, including measles, mumps, rubella, Hepatitis B, Epstein-Barr Virus (EBV), and *H. pylori.*

The effectiveness of each of these various types of antigen-specific avian transfer factors in inducing early secondary, or delayed-type hypersensitivity, immune responses in mammals was then tested by way of mouse footpad assays. Each type of antigen-specific avian transfer factor was tested using four different populations of mice, including a positive control population, a first test population, a second test population, and a negative control population, which were prepared as described previously herein with reference to FIG. 4. The mouse footpad assay for each type of antigen-specific transfer factor was conducted in accordance with the teachings of Petersen E A, Greenberg L E, Manzara T, and Kirkpatrick C H, "Murine transfer factor," I. Description of the model and evidence for specificity, J. Immunol., 126: 2480–84 (1981), the disclosure of which is hereby incorporated by this reference in its entirety.

In each mouse footpad assay, four populations of mice were prepared in the manner described in reference to FIG. 4.

In conducting the various mouse footpad assays on each of a positive control, a first and a second test, and a negative control populations, each mouse was anesthetized with isofluorane, the largest footpad of the left hind footpad of each mouse, which served as a control, was injected with about 0.01 ml of sterile saline diluent, and the largest footpad of the right hind foot of each mouse was injected with about 0.01 ml of a solution including the antigen or pathogen for which the avian transfer factor was specific.

About sixteen (16) to about twenty-four (24) hours following the hind footpad injections, each of the mice of the positive control, test, and negative control populations was again anesthetized with isoflurane and the sizes of the left and right hind footpads of each of the mice were again measured, for example, with a Starrett Gauge.

EXAMPLE 5

Using the same procedures described in EXAMPLES 1–3, avian transfer factor and avian antibodies specific for measles, mumps, and rubella (MMR) vaccine were generated in hens. Each hen received one dose of Merck MMR II vaccine, as described in EXAMPLE 1, at 150 days, 163 days, 190 days, 221 days, and 249 days. Eggs were collected from these hens just after the third innoculation-sometime in the period of about day 192 to about day 223 and prepared as described in EXAMPLE 1. This was done in this EXAMPLE and in the following EXAMPLES to ensure that a high level of transfer factor was present in the eggs. It is believed that transfer factor will be present in eggs about seven (7) days following the first innoculation.

A positive control population of mice was prepared about seven (7) days prior to the beginning of the mouse footpad assay by injecting each mouse of the positive control population with Merck MMR II vaccine, as described previously herein in reference to FIG. 4.

A solution containing both avian antibody and avian transfer factor specific for MMR vaccine was made by reconstituting in distilled water a lyophylized preparation similar to that described in EXAMPLE 2 to a concentration of about 8%, by weight. This transfer factor- and antibody-containing solution was administered to the first test population of mice in the manner described in reference to FIG. 4.

Lyophilized avian transfer factor specific for measles, mumps, and rubella, prepared by a method similar to that described in EXAMPLE 3, was reconstituted in distilled water to a concentration of about 8%, by weight. This reconstituted MMR-specific avian transfer factor was then administered to a second test population of mice in the manner described previously herein in reference to FIG. 4.

About 0.1 ml of a dose of Merck MMR II Vaccine was then administered to the largest footpad of the right hind foot of each mouse of each of positive control, first test, second test, and negative control populations, while substantially the same amount of sterile saline diluent was administered to the largest footpad of the left hind foot of each mouse, as described in reference to FIG. 4.

About sixteen (16) to about twenty-four (24) hours later, the mice were again anesthetized and the sizes of the largest footpads of both hind feet of each mouse measured, as previously described. The results follow:

TABLE 2

| MMR Vaccine-First Test Population (Antibody and Transfer Factor Administered) | | | |
|---|---|---|---|
| | Footpad size (μm): | | |
| | Before Sample Injection (0 hrs.) | Final (24 hrs.) | Difference |
| Mouse #1 | | | |
| Left Foot (Control) | 2159.00 | 2235.20 | 76.20 |
| Right Foot (Test) | 2133.60 | 2387.60 | 254.00 |

TABLE 2-continued MMR Vaccine-First Test Population (Antibody and Transfer Factor Administered)

Footpad size (μm):

|  | Before Sample Injection (0 hrs.) | Final (24 hrs.) | Difference |
|---|---|---|---|
| Mouse #2 | | | |
| Left Foot (Control) | 2133.60 | 2159.00 | 25.40 |
| Right Foot (Test) | 2133.60 | 2184.40 | 50.80 |
| Mouse #3 | | | |
| Left Foot (Control) | 2159.00 | 2159.00 | 0.00 |
| Right Foot (Test) | 2159.00 | 2184.40 | 25.40 |
| Mouse #4 | | | |
| Left Foot (Control) | 2209.80 | 2235.20 | 25.40 |
| Right Foot (Test) | 2286.00 | 2311.40 | 25.40 |
| Mouse #5 | | | |
| Left Foot (Control) | 2184.40 | 2184.40 | 0.00 |
| Right Foot (Test) | 2209.80 | 2260.60 | 50.80 |
| Mouse #6 | | | |
| Left Foot (Control) | 2260.60 | 2336.80 | 76.20 |
| Right Foot (Test) | 2235.20 | 2438.40 | 203.20 |

The data for Mouse #6 may have been inaccurate since the scabs from bite marks were present on one or both hind footpads of this mouse at the time the second measurements were taken (i.e., at about sixteen (16) to about twenty-four (24) hours). Nonetheless, with the exception of Mouse #4, each of the remaining mice of the first test population exhibited greater swelling at the time the second footpad measurements were taken in the footpads that were injected with the MMR II vaccine than in the footpads that were injected with the control solution. In Mouse #4, the amount of swelling was about the same in both the left and right footpads.

Overall, as can be seen from the data of TABLE 2, the largest footpads of the right feet of the first test population of mice represented exhibited an average of about 67.73 μm more swelling than the amount of swelling of the largest footpad of the left feet of these mice.

TABLE 3

MMR Vaccine-Second Test Population (Only Transfer Factor Administered)

Footpad size (μm):

|  | Before Sample Injection (0 hrs.) | Final (24 hrs.) | Difference |
|---|---|---|---|
| Mouse #1 | | | |
| Left Foot (Control) | 2082.80 | 2133.60 | 50.80 |
| Right Foot (Test) | 2108.20 | 2235.20 | 127.00 |
| Mouse #2 | | | |
| Left Foot (Control) | 2336.80 | 2387.60 | 50.80 |
| Right Foot (Test) | 2387.60 | 2641.60 | 254.00 |
| Mouse #3 | | | |
| Left Foot (Control) | 2184.40 | 2184.40 | 0.00 |
| Right Foot (Test) | 2184.40 | 2311.40 | 127.00 |
| Mouse #4 | | | |
| Left Foot (Control) | 2133.60 | 2133.60 | 0.00 |
| Right Foot (Test) | 2133.60 | 2133.60 | 0.00 |
| Mouse #5 | | | |
| Left Foot (Control) | 2082.80 | 2540.00 | 457.20 |
| Right Foot (Test) | 2108.20 | 2235.20 | 127.00 |
| Mouse #6 | | | |
| Left Foot (Control) | 2260.60 | 2286.00 | 25.40 |
| Right Foot (Test) | 2286.00 | 2362.20 | 76.20 |

As scabs from bite marks were visible on the footpads of Mouse #2 and Mouse #5 at about twenty-four hours following the injection of antigen and sample, the data form these mice may have been inaccurate. In addition, the largest footpad on the left foot of Mouse #5 was swollen more than three times as much as the corresponding footpad on the left foot of Mouse #5 and several times more than the swelling that occurred in any of the footpads of the other tested mice. Accordingly, the swelling data obtained from Mouse #5 were also omitted as this swelling in the footpad of the left foot was excessive. No increase in swelling in either footpad was measured in Mouse #4. Nonetheless, each of Mouse #1, Mouse #3, and Mouse #6 exhibited greater swelling in the (right) footpad that was injected with the second, substantially antibody-free, transfer factor-containing solution than in the (left) footpad that was injected with the control solution.

Based on the data presented in TABLE 3, on average, the largest footpads on the right feet of Mice ## 1, 3, and 6 were swollen about 91.4 μm more than the largest footpads on the left feet of these mice.

TABLE 4

MMR Vaccine-Positive Control

Footpad size (μm):

|  | Before Sample Injection (0 hrs.) | Final (24 hrs.) | Difference |
|---|---|---|---|
| Mouse #1 | | | |
| Left Foot (Control) | 2184.40 | 2235.20 | 50.80 |
| Right Foot (Test) | 2184.40 | 2260.60 | 76.20 |
| Mouse #2 | | | |
| Left Foot (Control) | 2184.40 | 2209.80 | 25.40 |
| Right Foot (Test) | 2184.40 | 2209.80 | 25.40 |
| Mouse #3 | | | |
| Left Foot (Control) | 2006.60 | 2133.60 | 127.00 |
| Right Foot (Test) | 1981.20 | 2108.20 | 127.00 |
| Mouse #4 | | | |
| Left Foot (Control) | 2133.60 | 2184.40 | 50.80 |
| Right Foot (Test) | 2133.60 | 2260.60 | 127.00 |

TABLE 4-continued

MMR Vaccine-Positive Control

Footpad size (μm):

| | Before Sample Injection (0 hrs.) | Final (24 hrs.) | Difference |
|---|---|---|---|
| Mouse #5 | | | |
| Left Foot (Control) | 2108.20 | 2133.60 | 25.40 |
| Right Foot (Test) | 2108.20 | 2286.00 | 177.80 |
| Mouse #6 | | | |
| Left Foot (Control) | 2082.80 | 2133.60 | 50.80 |
| Right Foot (Test) | 2057.40 | 2209.80 | 152.40 |

While Mouse #2 and Mouse #3 of the positive control population both exhibited substantially the same amount of swelling in the largest footpads of both the left and right hind feet, each of the other mice had a greater amount of swelling in the largest footpads of their right hind feet and, thus, displayed a secondary immune response to the MMR vaccine that was introduced into the largest footpads of their right hind feet, than the amount of swelling in the largest footpads of the left hind feet of these mice, which were much less swollen.

Based on the data in TABLE 4, it is apparent that the average amount of swelling in the largest footpads of the right hind feet of these mice was about 59.27 μm greater than the swelling of the largest footpads on the left hind feet of these mice.

TABLE 5

MMR Vaccine-Negative Control

Footpad size (μm):

| | Before Sample Injection (0 hrs.) | Final (24 hrs.) | Difference |
|---|---|---|---|
| Mouse #1 | | | |
| Left Foot (Control) | 2159.00 | 2159.00 | 0.00 |
| Right Foot (Test) | 2159.00 | 2209.80 | 50.80 |
| Mouse #2 | | | |
| Left Foot (Control) | 2159.00 | 2159.00 | 0.00 |
| Right Foot (Test) | 2108.20 | 2133.60 | 25.40 |
| Mouse #3 | | | |
| Left Foot (Control) | 2133.60 | 2133.60 | 0.00 |
| Right Foot (Test) | 2133.60 | 2133.60 | 0.00 |
| Mouse #4 | | | |
| Left Foot (Control) | 2108.20 | 2133.60 | 25.40 |
| Right Foot (Test) | 2108.20 | 2108.20 | 0.00 |
| Mouse #5 | | | |
| Left Foot (Control) | 2057.40 | 2057.40 | 0.00 |
| Right Foot (Test) | 2032.00 | 2032.00 | 0.00 |
| Mouse #6 | | | |
| Left Foot (Control) | 2082.80 | 2133.60 | 50.80 |
| Right Foot (Test) | 2032.00 | 2082.80 | 50.80 |

Two of the mice, Mouse #3 and Mouse #5, of the negative control population exhibited no swelling in the largest footpad of either hind foot. The largest footpads on both hind feet of Mouse #6 were swollen by about the same amount. While the largest footpads on the left hind feet of Mouse #1 and Mouse #4 were not swollen and the footpads on the right hind feet of these two mice were slightly swollen, the largest footpad on the right hind foot of Mouse #4 was not swollen and the largest left hind footpad was only slightly swollen. In fact, the average amount of swelling in the largest footpads of the right hind feet of these mice was only about 8.47 μm greater than the amount of swelling measured in the largest footpads of the left hind feet of the negative control population of mice. Consequently, the data in TABLE 5 indicate that the mice of the negative control population did not elicit a secondary immune response to the MMR vaccine.

Collectively, the data of TABLES 2–5 indicate that a secondary, or delayed-type hypersensitivity, immune response occurred in the majority of mice in each of the first test population, the second test population, and the positive control population, while no such secondary immune response appeared to be present in the negative control population. Accordingly, the data in TABLES 2 and 3 indicate that avian transfer factor specific for MMR vaccine, as well as avian antibody specific for MMR vaccine, are capable of inducing an early secondary immune response in mammals.

EXAMPLE 6

Repeating the procedures described previously herein in EXAMPLES 1–3, avian transfer factor and avian antibodies specific for the Hepatitis B virus were generated by use of a synthetic Hepatitis B antigen vaccine sold under the tradename ENGERIX-B. Each hen received one dose of the Hepatitis B vaccine, as described in EXAMPLE 1, at 150 days, 163 days, 190 days, 221 days, and 249 days. Eggs were collected from these hens sometime in the period of about day 193 and about day 223, as described in EXAMPLE 1 above, and prepared as described in EXAMPLE 1.

A positive control population of mice was prepared about seven (7) days prior to conducting the mouse footpad assay by injecting each mouse of the positive control population with the synthetic Hepatitis B vaccine, ENGERIX-B in the manner described in reference to FIG. 4.

A first solution, which included both avian antibody and avian transfer factor that were specific for Hepatitis B vaccine, was made by reconstituting in distilled water a lyophilized preparation similar to that described in EXAMPLE 2 to a concentration of about 16%, by weight. This transfer factor- and antibody-containing solution was administered to a first test population of mice in the manner described in reference to FIG. 4.

In addition, lyophilized avian transfer factor specific for Hepatitis B vaccine, which was prepared in a similar manner to that described in EXAMPLE 3, was reconstituted in distilled water to a concentration of about 16%, by weight. The reconstituted transfer factor-containing solution was then administered to each of the mice of a second test population, as explained previously herein in reference to FIG. 4.

At the appropriate time, the synthetic Hepatitis B vaccine was administered to the largest footpad of the right foot of each mouse of each of the positive control, first test, second test, and negative control populations, as described previously herein in reference to FIG. 4. The largest footpad of the left foot of each mouse of the four populations was substantially concurrently injected with the same amount of sterile saline diluent, also as described previously herein.

About sixteen (16) to about twenty-four (24) hours later, each of the mice of the four populations was again anesthetized and the sizes of the largest footpads of both hind feet of each mouse were again measured, as described previously herein. The results follow:

TABLE 6

Hepatitis B Vaccine - First Test Population
(Antibody and Transfer Factor Administered)

Footpad size (μm):

| | Before Sample Injection (0 hrs.) | Final (24 hrs.) | Difference |
|---|---|---|---|
| Mouse #1 | | | |
| Left Foot (Control) | 2032.00 | 2108.20 | 76.20 |
| Right Foot (Test) | 2032.00 | 2082.80 | 50.80 |
| Mouse #2 | | | |
| Left Foot (Control) | 2260.60 | 2362.20 | 101.60 |
| Right Foot (Test) | 2209.80 | 2336.80 | 127.00 |
| Mouse #3 | | | |
| Left Foot (Control) | 2159.00 | 2184.40 | 25.40 |
| Right Foot (Test) | 2159.00 | 2235.20 | 76.20 |
| Mouse #4 | | | |
| Left Foot (Control) | 2108.20 | 2184.40 | 76.20 |
| Right Foot (Test) | 2108.20 | 2260.60 | 152.40 |
| Mouse #5 | | | |
| Left Foot (Control) | 1930.40 | 2032.00 | 101.60 |
| Right Foot (Test) | 1930.40 | 2108.20 | 177.80 |
| Mouse #6 | | | |
| Left Foot (Control) | 2184.40 | 2184.40 | 0.00 |
| Right Foot (Test) | 2184.40 | 2235.20 | 50.80 |

Each of the mice of the first test population, with the exception of Mouse #1, exhibited greater swelling in the largest footpad of the right hind foot. On average, the largest footpads of the right hind feet of the mice of the first test population were about 42.17 μm more swollen than the largest footpads of the left hind feet of these mice. Thus, the data of TABLE 6 indicate that the avian transfer factor in the preparation that included transfer factor and antibody specific for the synthetic Hepatitis B vaccine induced an early secondary immune response in each of these mice.

TABLE 7

Hepatitis B Vaccine - Second Test Population
(Only Transfer Factor Administered)

Footpad size (μm):

| | Before Sample Injection (0 hrs.) | Final (24 hrs.) | Difference |
|---|---|---|---|
| Mouse #1 | | | |
| Left Foot (Control) | 1981.20 | 2032.00 | 50.80 |
| Right Foot (Test) | 2006.60 | 2159.00 | 152.40 |
| Mouse #2 | | | |
| Left Foot (Control) | 1981.20 | 1981.20 | 0.00 |
| Right Foot (Test) | 1981.20 | 2006.60 | 25.40 |
| Mouse #3 | | | |
| Left Foot (Control) | 2006.60 | 2032.00 | 25.40 |
| Right Foot (Test) | 2032.00 | 2082.80 | 50.80 |

TABLE 7-continued

Hepatitis B Vaccine - Second Test Population
(Only Transfer Factor Administered)

Footpad size (μm):

| | Before Sample Injection (0 hrs.) | Final (24 hrs.) | Difference |
|---|---|---|---|
| Mouse #4 | | | |
| Left Foot (Control) | 1955.80 | 2133.60 | 177.80 |
| Right Foot (Test) | 1981.20 | 2108.20 | 127.00 |
| Mouse #5 | | | |
| Left Foot (Control) | 1930.40 | 2006.60 | 76.20 |
| Right Foot (Test) | 1930.40 | 2057.40 | 127.00 |
| Mouse #6 | | | |
| Left Foot (Control) | 2032.00 | 2057.40 | 25.40 |
| Right Foot (Test) | 2006.60 | 2108.20 | 101.60 |

On average the largest footpads on the right hind feet of the second test population of mice were about 38.10 μm more swollen than the largest footpads on the left hind feet of these mice. With the exception of Mouse #4, the data of TABLE 7 illustrate that the administration of avian transfer factor specific for Hepatitis B vaccine induced an early secondary, or delayed-type hypersensitivity, immune response in the largest footpad of the right hind foot of each mouse.

TABLE 8

Hepatitis B Vaccine - Positive Control

Footpad size (μm):

| | Before Sample Injection (0 hrs.) | Final (24 hrs.) | Difference |
|---|---|---|---|
| Mouse #1 | | | |
| Left Foot (Control) | 2108.20 | 2133.60 | 25.40 |
| Right Foot (Test) | 2108.20 | 2159.00 | 50.80 |
| Mouse #2 | | | |
| Left Foot (Control) | 2032.00 | 2082.80 | 50.80 |
| Right Foot (Test) | 2006.60 | 2108.20 | 101.60 |
| Mouse #3 | | | |
| Left Foot (Control) | 1854.20 | 1930.40 | 76.20 |
| Right Foot (Test) | 1879.60 | 2032.00 | 152.40 |
| Mouse #4 | | | |
| Left Foot (Control) | 2006.60 | 2108.20 | 101.60 |
| Right Foot (Test) | 2057.40 | 2209.80 | 152.40 |
| Mouse #5 | | | |
| Left Foot (Control) | 2133.60 | 2159.00 | 25.40 |
| Right Foot (Test) | 2133.60 | 2159.00 | 25.40 |
| Mouse #6 | | | |
| Left Foot (Control) | 2006.60 | 2133.60 | 127.00 |
| Right Foot (Test) | 2006.60 | 2184.40 | 177.80 |

In the positive control population of mice, only Mouse #5 failed to elicit a secondary immune response to the synthetic Hepatitis B vaccine. The largest footpads on the right hind feet of each of the other mice of the positive control population exhibited an average of about 42.33 μm increased swelling over that of the largest footpads on the left hind feet of these mice.

TABLE 9

Hepatitis B Vaccine - Negative Control

| | Footpad size (μm): | | |
|---|---|---|---|
| | Before Sample Injection (0 hrs.) | Final (24 hrs.) | Difference |
| Mouse #1 | | | |
| Left Foot (Control) | 2159.00 | 2159.00 | 0.00 |
| Right Foot (Test) | 2133.60 | 2133.60 | 0.00 |
| Mouse #2 | | | |
| Left Foot (Control) | 2057.40 | 2057.40 | 0.00 |
| Right Foot (Test) | 2082.80 | 2082.80 | 0.00 |
| Mouse #3 | | | |
| Left Foot (Control) | 2006.60 | 2032.00 | 25.40 |
| Right Foot (Test) | 1955.80 | 2032.00 | 72.60 |
| Mouse #4 | | | |
| Left Foot (Control) | 2057.40 | 2082.80 | 25.40 |
| Right Foot (Test) | 2057.40 | 2108.20 | 50.80 |
| Mouse #5 | | | |
| Left Foot (Control) | 2133.60 | 2133.60 | 0.00 |
| Right Foot (Test) | 2133.60 | 2159.00 | 25.40 |
| Mouse #6 | | | |
| Left Foot (Control) | 2082.80 | 2133.60 | 50.80 |
| Right Foot (Test) | 2082.80 | 2133.60 | 50.80 |

Three mice of the negative control population exhibited substantially the same amount of swelling in the largest footpads of both the left and right hind feet. Of the remaining three mice, only mouse #3 exhibited a significantly greater amount of swelling in the largest food pad of her right hind foot than in her left hind foot. On average, the difference in swelling between the largest footpads on the right and left hind feet of the mice of the negative control population was only about 16.33 μm.

Collectively, the data presented in TABLES 6–9 indicate the result of EXAMPLE 6 to be that both avian antibody and avian transfer factor specific for synthetic Hepatitis B vaccine cause mammals to elicit an early secondary immune response to the antigen of the synthetic Hepatitis B vaccine, which is also presented by the Hepatitis B virus.

EXAMPLE 7

Again employing substantially the same procedures outlined above in EXAMPLES 1–3, avian transfer factor and avian antibody specific for the *H. pylori* bacteria were generated in hens. Each of the hens was infected with the *H. pylori* EIA antigen, in a manner similar to that described in EXAMPLE 1, at day 150, day 163, day 190, day 221, and day 249. Eggs were collected from these hens during the period of about day 193 to about day 223, as described in EXAMPLE 1, and prepared, as described in EXAMPLE 1.

As in the previous EXAMPLES, a positive control population of mice was prepared about seven (7) days prior to conducting the mouse footpad assay by injecting each of the mice of the positive control population with the recombinant, or synthetic, *H. pylori* EIA antigen, as described in reference to FIG. 4.

A solution including both avian antibody and avian transfer factor specific for the *H. pylori* EIA antigen was made by reconstituting in distilled water a lyophilized preparation including such avian antibody and avian transfer factor, similar to the preparation described above in EXAMPLE 2, to a concentration of about 16%, by weight. This solution was administered to a first test population of mice, as described previously herein in reference to FIG. 4.

A substantially antibody-free solution including avian transfer factor specific for *H. pylori* was prepared by reconstituting a lyophilized preparation, obtained in a manner similar to that described in EXAMPLE 3, in distilled water to a concentration of about 16%, by weight. This substantially antibody-free avian transfer factor-containing solution was then administered to each of the mice of a second test population, as described previously herein in reference to FIG. 4.

The largest footpad of the right foot of each mouse of each of the positive control, first test, second test, and negative control populations, was infected with *H. pylori* EIA antigen, while the same amount of sterile saline diluent was administered to the largest footpad of the left foot of each of these mice in the manner detailed previously herein in reference to FIG. 4.

At the appropriate time, about sixteen (16) to about twenty-four (24) hours following the infection of the largest footpads of the right feet of the mice with *H. pylori*, the mice were again anesthetized and the sizes of the largest footpads of both hind feet of each mouse was measured, as described previously herein. The results follow:

TABLE 10

H. Pylori - First Test Population
(Antibody and Transfer Factor Administered)

| | Footpad size (μm): | | |
|---|---|---|---|
| | Before Sample Injection (0 hrs.) | Final (24 hrs.) | Difference |
| Mouse #1 | | | |
| Left Foot (Control) | 1955.80 | 1981.20 | 25.40 |
| Right Foot (Test) | 1930.40 | 1955.80 | 25.40 |
| Mouse #2 | | | |
| Left Foot (Control) | 2133.60 | 2133.60 | 0.00 |
| Right Foot (Test) | 2108.20 | 2260.60 | 152.40 |
| Mouse #3 | | | |
| Left Foot (Control) | 2082.80 | 2082.80 | 0.00 |
| Right Foot (Test) | 2108.20 | 2133.60 | 25.40 |
| Mouse #4 | | | |
| Left Foot (Control) | 2082.80 | 2184.40 | 101.60 |
| Right Foot (Test) | 2082.80 | 2286.00 | 203.20 |
| Mouse #5 | | | |
| Left Foot (Control) | 2108.20 | 2133.60 | 25.40 |
| Right Foot (Test) | 2133.60 | 2133.60 | 0.00 |
| Mouse #6 | | | |
| Left Foot (Control) | 1955.80 | 2032.00 | 76.20 |
| Right Foot (Test) | 1930.40 | 2108.20 | 177.80 |

The data of TABLE 10 and, particularly those of Mouse #2, Mouse #4, and Mouse #6, indicate that administration of the solution containing both avian antibody and avian transfer factor specific for *H. pylori* induced an early secondary immune response in the mice of the first test population. While Mouse #1 exhibited substantially equal amounts of swelling in the largest footpads of both her left and right hind feet, Mouse #3 exhibited slightly greater swelling in the largest footpad of her right hind foot than in that of her left hind foot and Mouse #5 exhibited a slightly greater amount of swelling in the largest footpad of her left hind foot than in the largest footpad of her right hind foot. On average, the largest footpads of the right hind feet of the mice of the first test population were about 59.27 μm more swollen than the largest footpads of the left hind feet of these mice.

TABLE 11

H. Pylori - Second Test Population
(Only Transfer Factor Administered)

| | Footpad size (μm): | | |
|---|---|---|---|
| | Before Sample Injection (0 hrs.) | Final (24 hrs.) | Difference |
| Mouse #1 | | | |
| Left Foot (Control) | 2235.20 | 2235.20 | 0.00 |
| Right Foot (Test) | 2184.40 | 2209.80 | 25.40 |
| Mouse #2 | | | |
| Left Foot (Control) | 2006.60 | 2006.60 | 0.00 |
| Right Foot (Test) | 2006.60 | 2032.00 | 25.40 |
| Mouse #3 | | | |
| Left Foot (Control) | 2082.80 | 2184.40 | 101.60 |
| Right Foot (Test) | 2133.60 | 2209.80 | 76.20 |
| Mouse #4 | | | |
| Left Foot (Control) | 2133.60 | 2133.60 | 0.00 |
| Right Foot (Test) | 2133.60 | 2159.00 | 25.40 |
| Mouse #5 | | | |
| Left Foot (Control) | 2159.00 | 2184.40 | 25.40 |
| Right Foot (Test) | 2159.00 | 2235.20 | 76.20 |
| Mouse #6 | | | |
| Left Foot (Control) | 2057.40 | 2082.80 | 25.40 |
| Right Foot (Test) | 2032.00 | 2260.60 | 228.60 |

The results shown in TABLE 11 were similar to those in TABLE 10. Two of the mice, Mouse #5 and Mouse #6, exhibited much more swelling in the largest footpads of their right hind feet than in the largest footpads of their left hind feet. While the amount of swelling in the largest footpads of the right hind feet of Mouse #1, Mouse #2, and Mouse #4 was greater than that of the largest footpads of the left hind feet of these mice, the difference was only slight. Mouse #3 actually exhibited a slightly greater amount of swelling in the largest footpad of her left hind foot than in the largest footpad of her right hind foot. Nonetheless, as the average swelling in the largest footpads of the right hind feet of these mice is, on average, about 50.80 μm greater than that of the largest footpads on the left hind feet of these mice, the data of TABLE 11 indicate that avian transfer factor specific for H. pylori caused the increased swelling.

TABLE 12

H. Pylori - Positive Control

| | Footpad size (μm): | | |
|---|---|---|---|
| | Before Sample Injection (0 hrs.) | Final (24 hrs.) | Difference |
| Mouse #1 | | | |
| Left Foot (Control) | 2133.60 | 2133.60 | 0.00 |
| Right Foot (Test) | 2108.20 | 2184.40 | 76.20 |

TABLE 12-continued

H. Pylori - Positive Control

| | Footpad size (μm): | | |
|---|---|---|---|
| | Before Sample Injection (0 hrs.) | Final (24 hrs.) | Difference |
| Mouse #2 | | | |
| Left Foot (Control) | 2133.60 | 2133.60 | 0.00 |
| Right Foot (Test) | 2133.60 | 2209.80 | 76.20 |
| Mouse #3 | | | |
| Left Foot (Control) | 2032.00 | 2108.20 | 76.20 |
| Right Foot (Test) | 2082.80 | 2209.80 | 127.00 |
| Mouse #4 | | | |
| Left Foot (Control) | 1981.20 | 2082.80 | 101.60 |
| Right Foot (Test) | 1879.60 | 2133.60 | 254.00 |
| Mouse #5 | | | |
| Left Foot (Control) | 2133.60 | 2159.00 | 25.40 |
| Right Foot (Test) | 2184.40 | 2336.80 | 152.40 |
| Mouse #6 | | | |
| Left Foot (Control) | 2133.60 | 2133.60 | 0.00 |
| Right Foot (Test) | 2082.80 | 2260.60 | 177.80 |

Each of the mice of the positive control population in EXAMPLE 7 elicited at delayed-type hypersensitivity immune response to H. pylori, as indicated by the significant differences in the amount of swelling in the largest footpads of the right hind feet of these mice relative to that in the largest footpads of the left hind feet of these mice. On average, the difference in swelling was about 110.07 μm.

TABLE 13

H. Pylori - Negative Control

| | Footpad size (μm): | | |
|---|---|---|---|
| | Before Sample Injection (0 hrs.) | Final (24 hrs.) | Difference |
| Mouse #1 | | | |
| Left Foot (Control) | 2006.60 | 2082.80 | 76.20 |
| Right Foot (Test) | 2514.60 | 2514.60 | 0.00 |
| Mouse #2 | | | |
| Left Foot (Control) | 2032.00 | 2082.80 | 50.80 |
| Right Foot (Test) | 2032.00 | 2133.60 | 101.60 |
| Mouse #3 | | | |
| Left Foot (Control) | 2082.80 | 2108.20 | 25.40 |
| Right Foot (Test) | 2082.80 | 2108.20 | 25.40 |
| Mouse #4 | | | |
| Left Foot (Control) | 2006.60 | 2032.00 | 25.40 |
| Right Foot (Test) | 1955.80 | 2032.00 | 76.20 |
| Mouse #5 | | | |
| Left Foot (Control) | 1930.40 | 1981.20 | 50.80 |
| Right Foot (Test) | 1955.80 | 2006.60 | 50.80 |
| Mouse #6 | | | |
| Left Foot (Control) | 2133.60 | 2159.00 | 25.40 |
| Right Foot (Test) | 2133.60 | 2159.00 | 25.40 |

As indicated by the data of TABLE 13, the amount of swelling in the largest footpads of both the left and right hind feet of Mouse #3, Mouse #5, and Mouse #6, were substantially the same. While the amount of swelling in the largest footpad of the right hind foot of Mouse #2 was greater than the amount of swelling in the largest footpad of the left hind foot of that mouse, the largest footpad of the left hind foot of Mouse #1 was significantly more swollen than the largest footpad of the right hind foot of Mouse #1. The largest footpad of the right hind foot of Mouse #4 was only slightly more swollen than the largest footpad of the left hind foot of Mouse #4. The average difference in swelling of the largest footpads of the right and left hind feet of the mice of the negative control population was only about 4.23 μm.

The data of TABLES 10–13 indicate that avian transfer factor specific for *H. pylori* facilitates an early secondary immune response in mammals.

EXAMPLE 8

Again, employing substantially the same procedures described previously herein in EXAMPLES 1–3, avian transfer factor and avian antibody specific for the EBNA-1 antigen, a recombinant nuclear antigen of the Epstein-Barr virus (EBV), were generated in hens. Each hen received one dose of EBNA-1, such as described in EXAMPLE 1, at 150 days, 163 days, 190 days, and 249 days. Eggs were collected from these hens during the period of about day 193 to about day 223, as described above in EXAMPLE 1, and prepared as described above in EXAMPLE 1.

A solution with both avian antibody and avian transfer factor specific for EBNA-1 was formed by reconstituting in distilled water a lyophilized preparation similar to that described in EXAMPLE 2. The lyophilized preparation including both avian antibody and avian transfer factor specific for EBNA-1 antigen was diluted to a concentration of about 16%, by weight. This solution was then administered to a first test population of mice in the manner described in reference to FIG. 4.

In addition, a solution containing avian transfer factor specific for EBNA-1, with substantially no avian antibody specific for EBNA-1, was also reconstituted in distilled water to a concentration of about 16%, by weight. This solution was administered to the mice of a second test population in the manner described previously herein in reference to FIG. 4.

A positive control population of mice was prepared by injecting mice with EBNA-1 about seven (7) days before conducting the mouse footpad assay.

Recombinant EBNA-1 antigen was then administered to the largest footpad of the right hind foot of each mouse of each of four populations, including a first test population, a second test population, a positive control population, and a negative control population. Substantially the same amount of sterile saline diluent was administered to the largest footpad of the left hind foot of each mouse. The method of administration was conducted in the same manner as that described previously herein.

About sixteen (16) to about twenty-four (24) hours later, the mice were again anesthetized and the sizes of the largest footpads of both hind feet of each mouse measured, as previously described. The results follow:

TABLE 14

EBV EBNA-1 - First Test Population
(Antibody and Transfer Factor Administered)

Footpad size (μm):

|  | Before Sample Injection (0 hrs.) | Final (24 hrs.) | Difference |
|---|---|---|---|
| Mouse #1 | | | |
| Left Foot (Control) | 2032.00 | 2057.40 | 25.40 |
| Right Foot (Test) | 2032.00 | 2057.40 | 25.40 |
| Mouse #2 | | | |
| Left Foot (Control) | 2159.00 | 2159.00 | 0.00 |
| Right Foot (Test) | 2159.00 | 2184.40 | 25.40 |
| Mouse #3 | | | |
| Left Foot (Control) | 2159.00 | 2159.00 | 0.00 |
| Right Foot (Test) | 2133.60 | 2286.00 | 152.40 |
| Mouse #4 | | | |
| Left Foot (Control) | 2108.20 | 2108.20 | 0.00 |
| Right Foot (Test) | 2108.20 | 2209.80 | 101.60 |
| Mouse #5 | | | |
| Left Foot (Control) | 2108.20 | 2235.20 | 127.00 |
| Right Foot (Test) | 2082.80 | 2260.60 | 177.80 |
| Mouse #6 | | | |
| Left Foot (Control) | 1981.20 | 2032.00 | 50.80 |
| Right Foot (Test) | 1981.20 | 2032.00 | 50.80 |

In TABLE 14, it is seen that three of the mice exhibited significantly greater swelling in the largest footpads of their right hind feet than in the largest footpads of their left hind feet. While Mouse #2 also had a greater amount of swelling in the largest footpad of her right hind foot than that in the largest footpad of her left hind foot, the difference was only slight. Two of the mice, Mouse #1 and Mouse #6, had substantially the same amount of swelling in the largest footpads of both their left and right hind feet. Nonetheless, as the amount of swelling in the largest footpads of the right hind feet of the mice of the first test population exceeded that of the largest footpads of the left hind feet of these mice by an average of about 55.03 μm, the data presented in TABLE 14 tend to show that the avian transfer factor in the solution containing both avian antibody and transfer factor specific for EBNA-1 caused the mice of the first test population to elicit an early secondary immune response to the recombinant EBNA-1. As is known in the art, antibodies are passive with respect to secondary immune responses and typically contribute very little to swelling.

TABLE 15

EBV EBNA-1 - Second Test Population
(Only Transfer Factor Administered)

Footpad size (μm):

|  | Before Sample Injection (0 hrs.) | Final (24 hrs.) | Difference |
|---|---|---|---|
| Mouse #1 | | | |
| Left Foot (Control) | 2133.60 | 2159.00 | 25.40 |
| Right Foot (Test) | 2108.20 | 2159.00 | 50.80 |

TABLE 15-continued

EBV EBNA-1 - Second Test Population
(Only Transfer Factor Administered)

Footpad size (μm):

| | Before Sample Injection (0 hrs.) | Final (24 hrs.) | Difference |
|---|---|---|---|
| Mouse #2 | | | |
| Left Foot (Control) | 2006.60 | 2032.00 | 25.40 |
| Right Foot (Test) | 1955.80 | 1955.80 | 0.00 |
| Mouse #3 | | | |
| Left Foot (Control) | 2032.00 | 2133.60 | 101.60 |
| Right Foot (Test) | 2006.60 | 2159.00 | 152.40 |
| Mouse #4 | | | |
| Left Foot (Control) | 2108.20 | 2133.60 | 25.40 |
| Right Foot (Test) | 2159.00 | 2159.00 | 0.00 |
| Mouse #5 | | | |
| Left Foot (Control) | 2184.40 | 2209.80 | 25.40 |
| Right Foot (Test) | 2159.00 | 2260.60 | 101.60 |
| Mouse #6 | | | |
| Left Foot (Control) | 2057.40 | 2108.20 | 50.80 |
| Right Foot (Test) | 2082.80 | 2133.60 | 50.80 |

The mice of the second test population, which were treated with the avian transfer factor-containing solution also exhibited an early secondary immune response to recombinant EBNA-1. This result was particularly evident in Mouse #3 and Mouse #5, which exhibited significantly greater swelling in the largest footpads of their right hind feet than that measured in the largest footpads of their left hind feet. While the amount of swelling in the largest footpad of the right hind foot of Mouse #1 was also greater than the amount of swelling in the largest footpad of the left hind foot of Mouse #1, the difference appears to be slight. Moreover, while Mouse #2 and Mouse #4 displayed a greater amount of swelling in the largest footpads of their left hind feet, the amounts of swelling measured therein were only slightly greater than that measured in the largest footpads of the right hind feet of these mice. On average, the largest footpads of the right hand feet of these mice was about 16.93 μm greater than that measured in the largest footpads of the left hind feet of these mice.

It is believed that transfer factor specific for EBNA-1 may have become unstable when isolated from the corresponding antibody, resulting in the lower measured secondary immune response in the second test population relative to the overall secondary immune response measured in the first test population of mice.

TABLE 16

EBV EBNA-1 - Positive Control

Footpad size (μm):

| | Before Sample Injection (0 hrs.) | Final (24 hrs.) | Difference |
|---|---|---|---|
| Mouse #1 | | | |
| Left Foot (Control) | 2209.80 | 2209.80 | 0.00 |
| Right Foot (Test) | 2235.20 | 2286.00 | 50.80 |

TABLE 16-continued

EBV EBNA-1 - Positive Control

Footpad size (μm):

| | Before Sample Injection (0 hrs.) | Final (24 hrs.) | Difference |
|---|---|---|---|
| Mouse #2 | | | |
| Left Foot (Control) | 2184.40 | 2184.40 | 0.00 |
| Right Foot (Test) | 2209.80 | 2260.60 | 50.80 |
| Mouse #3 | | | |
| Left Foot (Control) | 2159.00 | 2159.00 | 0.00 |
| Right Foot (Test) | 2133.60 | 2209.80 | 76.20 |
| Mouse #4 | | | |
| Left Foot (Control) | 2159.00 | 2336.80 | 177.80 |
| Right Foot (Test) | 2133.60 | 2362.20 | 228.60 |
| Mouse #5 | | | |
| Left Foot (Control) | 2133.60 | 2133.60 | 0.00 |
| Right Foot (Test) | 2082.80 | 2260.60 | 177.80 |
| Mouse #6 | | | |
| Left Foot (Control) | 2082.80 | 2082.80 | 0.00 |
| Right Foot (Test) | 2057.40 | 2209.80 | 152.40 |

As indicated by the greater amounts of swelling in the largest footpads of the right hind feet of each mouse of the positive control population than that of the largest footpads of the left hind feet of these mice, all six of the mice of the positive control population exhibited a delayed-type hypersensitivity immune response to the recombinant EBNA-1 antigen. The measured amount of swelling in the largest footpads of the right hind feet of each of these mice was, on average, about 93.13 μm greater than the measured amount of swelling in the largest footpads of the left hind feet of these mice.

TABLE 17

EBV EBNA-1 - Negative Control

Footpad size (μm):

| | Before Sample Injection (0 hrs.) | Final (24 hrs.) | Difference |
|---|---|---|---|
| Mouse #1 | | | |
| Left Foot (Control) | 2133.60 | 2184.40 | 50.80 |
| Right Foot (Test) | 2082.80 | 2133.60 | 50.80 |
| Mouse #2 | | | |
| Left Foot (Control) | 2133.60 | 2133.60 | 0.00 |
| Right Foot (Test) | 2159.00 | 2184.40 | 25.40 |
| Mouse #3 | | | |
| Left Foot (Control) | 2108.20 | 2108.20 | 0.00 |
| Right Foot (Test) | 2133.60 | 2133.60 | 0.00 |
| Mouse #4 | | | |
| Left Foot (Control) | 2082.80 | 2133.60 | 50.80 |
| Right Foot (Test) | 2159.00 | 2159.00 | 0.00 |
| Mouse #5 | | | |
| Left Foot (Control) | 2057.40 | 2082.86 | 25.40 |
| Right Foot (Test) | 1955.80 | 1981.20 | 25.40 |

TABLE 17-continued

EBV EBNA-1 - Negative Control

Footpad size (μm):

| | Before Sample Injection (0 hrs.) | Final (24 hrs.) | Difference |
|---|---|---|---|
| Mouse #6 | | | |
| Left Foot (Control) | 2108.20 | 2133.60 | 25.40 |
| Right Foot (Test) | 2108.20 | 2133.60 | 25.40 |

In the negative control population, only two of the mice, Mouse #2 and Mouse #4, exhibited different amounts of swelling in the largest footpads of their hind feet. While the amount of swelling in the largest footpad of the right hind foot of Mouse #2 was greater than that exhibited in the largest footpad of the left hind foot, the largest footpad of the left hind foot of Mouse #4 was more swollen than the largest footpad of the right hind foot of Mouse #4. In fact, on average, the largest footpads of the right hind feet of the mice of the negative control population were about 4.23 μm less swollen than the largest footpads of the left hind feet of these mice.

Again, the data of TABLES 14–17 illustrate that avian transfer factor specific for EBNA-1 cause mammals to elicit an early secondary immune response (i.e., within about twenty-four (24) hours as compared to the typical seven (7) to fourteen (14) day time period it takes a mammal to elicit a secondary immune response on its own) to EBNA-1 and viruses and other pathogens that present this antigen.

The foregoing EXAMPLES illustrate that, by way of contrast with the seven (7) to fourteen (14) day time period that it typically takes a mammalian host to elicit a secondary immune response to a pathogen or antigenic agent on its own, when an avian transfer factor incorporating teachings of the present invention has been administered, the mammalian host may elicit a secondary immune response within about twenty-four (24) hours.

The similarities of the differences between the measurements taken at the test and control footpads of each mouse in first and second test groups of each assay indicate that the secondary, or delayed-type hypersensitivity, immune response, was elicited primarily by the transfer factor, not the antibody, which is passive with respect to secondary immune responses and which typically contributes very little to swelling.

It is apparent from EXAMPLES 1–8 and the data generated thereby that avian transfer factor has the ability to generate an early secondary immune response in mammals. As one of skill in the art would readily recognize, avian transfer factor would also generate an early secondary immune response in various types of birds, as well as in reptiles, amphibians, and other non-mammalian species of animals.

As avian transfer factor initiates an early delayed-type hypersensitivity immune reaction in mice, it is reasonable for those of ordinary skill in the art to assume that transfer factor has the same effect in other mammals, including humans.

Although transfer factor was administered to mice in the preceding EXAMPLES by way of injection, it is also within the scope of the present invention to administer avian transfer factor to mammals by other routes. For example, avian transfer factor could be administered orally, by parenteral injection, or by parenteral methods other than injection, such as transdermally, or through the skin, by aerosol via the lungs, or by other methods known in the art. Oral administration of avian transfer factor to mammals is supported by the fact that mammalian mothers supply transfer factor to their newborn children by way of colostrum, which the newborns ingest orally. Transfer factor survives the conditions of both the stomach and the small intestine, where transfer factor is absorbed into the bloodstream of the mammalian newborn. Thus, transfer factor is known to survive the intestinal tracts of mammals. The ability of transfer factor to withstand the conditions of the digestive tracts of mammals was demonstrated in Kirkpatrick C H, "Activities and characteristics of transfer factors," Biotherapy, 9: 13–16 (1996), the disclosure of which is hereby incorporated by this reference in its entirety.

Although the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed is:

1. A method for obtaining transfer factor, comprising:
    exposing a non-mammalian source animal to at least one antigenic agent that will cause said non-mammalian source animal to elicit a T-cell mediated immune response;
    permitting said non-mammalian source animal to elicit a T-cell mediated immune response to said at least one antigenic agent;
    collecting at least one egg from said non-mammalian source animal following said T-cell mediated immune response, said at least one egg including transfer factor that transfer cellular immunity to a mammal in vivo and that includes transfer factor molecules having molecular weights of about 4,000 Da to about 5,000 Da.

2. The method of claim 1, wherein said exposing said non-mammalian source animal comprises exposing an avian source animal to said at least one antigenic agent.

3. The method of claim 2, wherein said exposing said avian source animal comprises exposing a hen to said at least one antigenic agent.

4. The method of claim 1, wherein said exposing said non-mammalian source animal to at least one antigenic agent comprises permitting said non-mammalian source animal to be exposed to its natural environment.

5. The method of claim 1, wherein said exposing comprises injecting said non-mammalian source animal with said at least one antigenic agent.

6. The method of claim 1, wherein said exposing is conducted in the presence of an adjuvant.

7. The method of claim 1, wherein said exposing is conducted with substantially no adjuvant.

8. The method of claim 1, wherein said exposing comprises exposing said non-mammalian source animal to Newcastle Virus.

9. The method of claim 1, wherein said exposing comprises exposing said non-mammalian source animal to measles-mumps-rubella vaccine.

10. The method of claim 1, wherein said exposing comprises exposing said non-mammalian source animal to hepatitis B vaccine.

11. The method of claim 1, wherein said exposing comprises exposing said non-mammalian source animal to an antigen of Epstein-Barr Virus.

12. The method of claim 11, wherein said exposing comprises exposing said non-mammalian source animal to a recombinant Epstein-Barr Virus vaccine.

13. The method of claim 1, wherein said exposing comprises exposing said non-mammalian source animal to an antigen of H. pylori.

14. The method of claim 13, wherein said exposing comprises exposing said non-mammalian source animal to a synthetic H. pylori vaccine.

15. The method of claim 1, wherein said exposing comprises exposing said non-mammalian source animal substantially concurrently to a plurality of antigens.

16. The method of claim 1, wherein said exposing comprises exposing said non-mammalian source animal to at least one of a live vaccine, an attenuated vaccine, a killed vaccine, a recombinant antigen, and a natural antigen.

17. The method of claim 1, wherein said exposing comprises exposing said non-mammalian source animal to at least one of a bacterial antigen and a viral antigen.

18. The method of claim 1, wherein said exposing comprises exposing said non-mammalian source animal to an antigen at least based on an antigen of a pathogen from a non-mammalian pathogen source.

19. The method of claim 1, wherein said collecting said at least one egg is effected at least about seven days after said exposing.

20. The method of claim 1, wherein said collecting said at least one egg is effected at least about fourteen days after said exposing.

21. The method of claim 1, further comprising collecting a water soluble fraction of said at least one egg.

22. The method of claim 21, wherein said collecting said water soluble fraction comprises collecting a water soluble fraction of a yolk of said at least one egg.

23. The method of claim 21, further comprising removing substantially all antibodies from said water soluble fraction.

24. A method for obtaining transfer factor specific for a systemic pathogen, comprising:

exposing a non-mammalian source animal to at least one antigenic agent for causing said non-mammalian source animal to illicit a T-cell mediated immune response to the systemic pathogen;

permitting said non-mammalian source animal to elicit a T-cell mediated immune response to said at least one antigenic agent, said T-cell mediated immune response resulting in generation of transfer factor specific for the systemic pathogen; and following said T-cell mediated immune response, collecting transfer factor specific for said systemic pathogen, which transfers cellular immunity to a mammal in vivo and includes transfer factor molecules having molecular weights of about 4,000 Da to about 5,000 Da, from at least one egg of said non-mammalian source animal.

25. The method of claim 24, wherein said collecting includes substantially purifying said transfer factor from other proteins or peptides of said at least one egg having molecular weights of greater than about 8,000 Da.

26. The method of claim 24, wherein said exposing comprises exposing said non-mammalian source animal to at least one antigenic agent that causes said non-mammalian source animal to illicit a secondary immune response against at least one of rubeola virus, rubella virus, mumps virus, hepatitis-B virus, Newcastle Virus, and Epstein-Barr Virus.

27. The method of claim 24, wherein said exposing comprises exposing said non-mammalian source animal to at least one of an MMR vaccine, a Newcastle Virus vaccine, a recombinant Epstein-Barr Virus vaccine, a substantially purified Epstein-Barr Virus antigen, and a recombinant hepatitis B vaccine.

28. The method of claim 1, wherein said collecting includes substantially purifying said transfer factor from other proteins or peptides of said at least one egg having molecular weights of greater than about 8,000 Da.

29. The method of claim 25, wherein substantially purifying transfer factor comprises causing said other proteins or peptides having molecular weights of greater than about 8,000 Da to precipitate from a solution including said transfer factor.

30. The method of claim 28, wherein said substantially purifying transfer factor comprises causing said other proteins or peptides having molecular weights of greater than about 8,000 Da to precipitate from a solution including said transfer factor.

* * * * *

UNITED STATES PATENT AND TRADEMARK OFFICE
CERTIFICATE OF CORRECTION

PATENT NO.    : 6,468,534 B1                                              Page 1 of 1
DATED         : October 22, 2002
INVENTOR(S)   : William J. Hennen and David T. Lisonbee It is certified that error appears in the above-identified patent and that said Letters Patent is hereby corrected as shown below:

<u>Title page,</u>
Item [56], References Cited, OTHER PUBLICATIONS, in "Klesius et al." change "transfoer" to -- Transfer --, change "Elmeria" to -- Eimeria --, and change "Tenalta" to -- tenalla --; and in "Glambrone et al." change "Glambrone" to -- Giambrone --

<u>Column 2,</u>
Lines 39 and 43, change "cites" to -- sites --

<u>Column 14,</u>
Line 24, change "form" to -- from --

<u>Column 22,</u>
Line 31, change "at" to -- a --

Signed and Sealed this

Twenty-fourth Day of June, 2003

JAMES E. ROGAN
*Director of the United States Patent and Trademark Office*